(12) United States Patent
Seligman

(10) Patent No.: US 6,246,911 B1
(45) Date of Patent: Jun. 12, 2001

(54) COCHLEAR IMPLANTS WITH OFFSET COILS FOR TRANSMISSION OF RADIO FREQUENCY LINKS

(76) Inventor: Peter Seligman, 107 Fawkner Street, Essendon, Victoria 3040 (AU)

( * ) Notice: Subject to any disclaimer, the term of this patent is extended or adjusted under 35 U.S.C. 154(b) by 0 days.

(21) Appl. No.: 09/346,254

(22) Filed: Jul. 1, 1999

(30) Foreign Application Priority Data

Feb. 8, 1999 (AU) .................................. 15493/99

(51) Int. Cl.$^7$ .................................................. A61N 1/36
(52) U.S. Cl. .................................................................. 607/61
(58) Field of Search ............................. 607/56, 57, 60, 607/61, 63, 30, 31, 33

(56) References Cited

U.S. PATENT DOCUMENTS

| 3,920,025 | * 11/1975 | Stasz et al. ........................ 128/423 |
| 4,532,930 | 8/1985 | Crosby et al. . |
| 4,654,880 | 3/1987 | Sontag . |

\* cited by examiner

*Primary Examiner*—William E. Kamm
(74) *Attorney, Agent, or Firm*—Gottlieb, Rackman & Reisman, P.C.

(57) ABSTRACT

In an implantable prosthesis system such as a cochlear implant, a pair of coils are used to exchange control and/or power signals between the external and internal components. The coils are offset or displaced laterally by a predetermined distance to reduce variations in the signal transmission due to the spacing between the external and internal components.

26 Claims, 5 Drawing Sheets

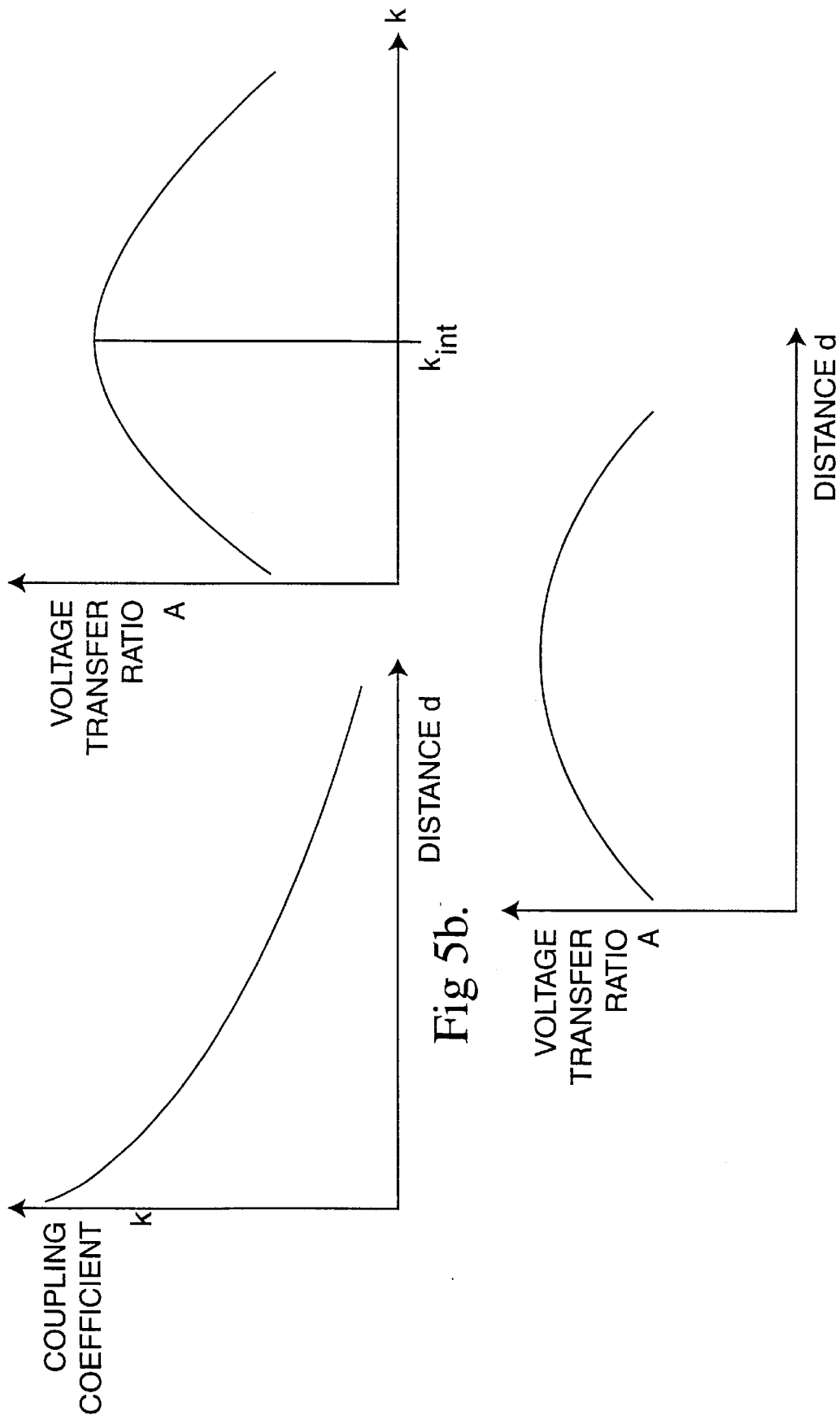

COCHLEAR IMPLANTS WITH OFFSET COILS FOR TRANSMISSION OF RADIO FREQUENCY LINKS

BACKGROUND OF THE INVENTION

A. Field of Invention

This invention pertains to transcutaneous tissue stimulating devices such as cochlear prostheses and functional electrical stimulators. Such devices are frequently of a two-part design, there being a part implanted within the body of the patient, for the purpose of providing therapy, and an external component in communication with the implanted part by means of a transcutaneous wireless link.

B. Description of the Prior Art

Implantable prosthesis devices are generally required to be small to reduce the trauma and other complications arising from the implantation and maintenance of foreign matter inside a patient's body. For example, cochlear implant systems typically include an external component and an internal component. The external component includes a microphone for sensing ambient sounds and a signal processor for generating stimulation signals corresponding to these sounds. The stimulation signals are transmitted to the internal component which applies the same to the aural nerve of the patient through an array of electrodes. Because the internal component may not have a permanent power supply, power for the component is also derived from the external component.

The means for providing both power and communication between the internal and external components is typically a pair of coils, one in the external component and one in the internal component. The coils are planar and are positioned parallel to each other so that energy is coupled through the skin and flesh of the patient from the external coil to the internal coil for the purpose of powering and/or controlling the internal component. Until now, the preferred arrangement for these coils was such that the voltage induced into the internal coil was very sensitive to variations in inter-coil distance.

Since the coils are separated by a partition comprising skin and tissue, the inter-coil distance is not constant from patient-to-patient but varies according to the anatomical characteristics of each implantee. A ramification of this variability is that in order to ensure that an adequate voltage level is induced in the internal coil, for purposes of operating the internal component of the cochlear implant, the voltage applied to the external coil must be sufficiently high to take into account patients having considerably thicker or thinner partition widths than typically encountered. As a consequence the voltage applied by the transmit coil is set to a relatively high value in order that the implanted portion will be supplied with sufficient power no matter the width of the implanteeÕs partition. Accordingly, an undesirable power wastage occurs in the majority of patients. A cochlear implant system of this kind is described in U.S. Pat. No. 4,532,930.

In a related known arrangement, tuned or tank circuits are used in the transmitter and receiver to transmit signals and power. In this arrangement, the critical parameter for power transmission is the coupling coefficient between the tuned circuit coils. This coupling coefficient is optimal only at a critical spacing between coils. One such system is disclosed in U.S. Pat. No. 4,654,880 to Sontag. Again, for optimal coupling, the two coils must be spaced at a critical distance from each other and must be co-axial. If the coils are not at the optimal distance, the signals are exchanged between the components at a low efficiency.

OBJECTIVES AND SUMMARY OF THE INVENTION

In view of the above, it is an objective of the present invention to provide an improved communication system for implantable devices which is less sensitive to variations in inter-coil spacing.

A further objective of the invention is to provide a transcutaneous tissue stimulation system such as a cochlear implant having coils positioned to obtain optimum power transfer characteristics.

A further objective is to provide a system which is easy and inexpensive to implement with minimal changes from the existing systems.

Other objectives and advantages of the invention shall become apparent from the following description.

Briefly, the subject invention provides a transcutaneous tissue stimulating system including:

a) an external portion for location on a first side of a partition, said external portion comprising a first coil for transmission of RF power, arranged to form an arc of a first radius and being mounted on a first coil platform said coil platform engaging a first magnet; and b) an internal portion for location on a side opposite the first side of said partition, comprising a second coil for receiving RF power, arranged to form an arc of a second radius said second coil being mounted on a second coil platform said second coil platform engaging a second magnet for attraction to said first magnet;

wherein the first and second coil, platform and magnets are arranged so that upon minimising the distance between said first and second magnets the centres of the first and second arcs are radially offset.

According to a further aspect of the invention there is provided a transcutaneous tissue stimulating system including:

a) an external portion for location on a first side of a partition, said external portion including a first coil for transmission of RF power, arranged to form an arc of a first radius and being retained by means of a first coil platform said coil platform engaging a first magnet in one of a first and a second selectable positions, said two selectable positions being radially offset from each other; and b) an internal portion for location on a side opposite the first side of said partition, comprising a second coil for receiving RF power, arranged to form an arc of a second radius said second coil being mounted on a second coil platform said second coil platform engaging a second magnet for attraction to said first magnet;

wherein the first and second coil, platform and magnets are arranged so that when said first magnet is engaged in said first selectable position then upon minimising the distance between said first and second magnets the centres of said first and second arcs are radially co-located and when said first magnet is engaged in said second selectable position then upon minimising said distance said centres are radially offset.

The invention operates to locate the paired coils relative to each other so as to reduce the sensitivity of the inter-coil voltage transfer ratio to variations in inter-coil distance as, will now be explained in more detail.

BRIEF DESCRIPTION OF THE DRAWINGS

FIG. 4 shows the relationship between the coupling coefficient and distance for the system of FIG. 3;

FIGS. 5A and 5B show respectively the relationships between a voltage transfer ratio A and the coupling coefficient, and the voltage transfer ratio A and distance for the system of FIG. 2 using the prior art coil positioning arrangement of FIGS. 1A and 1B;

DETAILED DESCRIPTION OF THE INVENTION

Figure 1A:
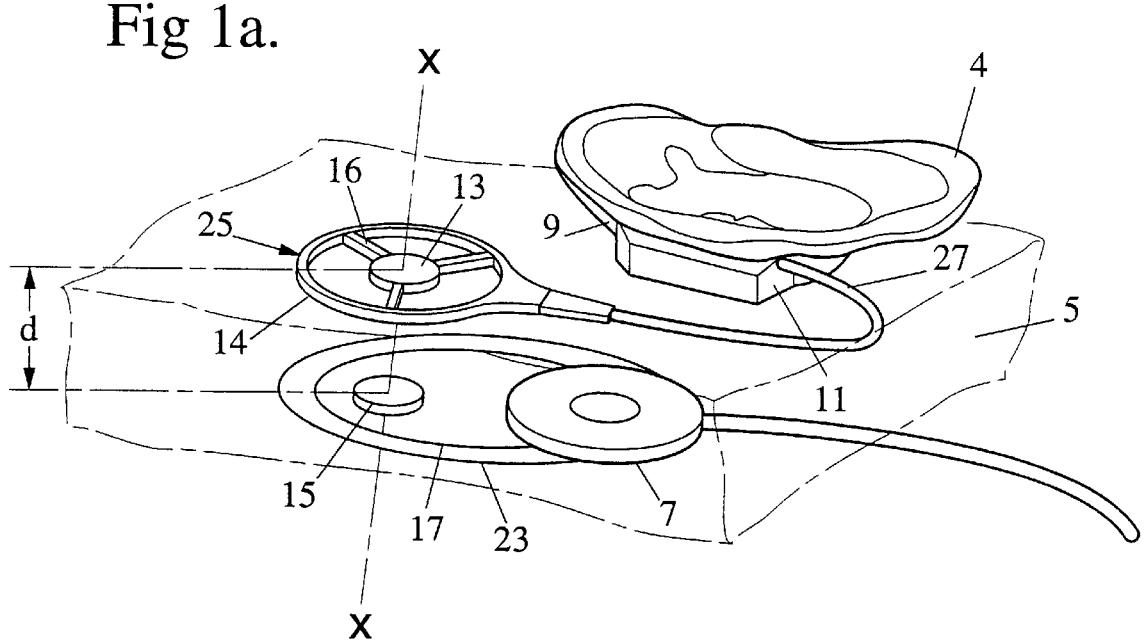
FIG. 1A shows a perspective schematic view of an arrangement of two coils for a first prior art implantable prosthesis system.
Figure 1B:
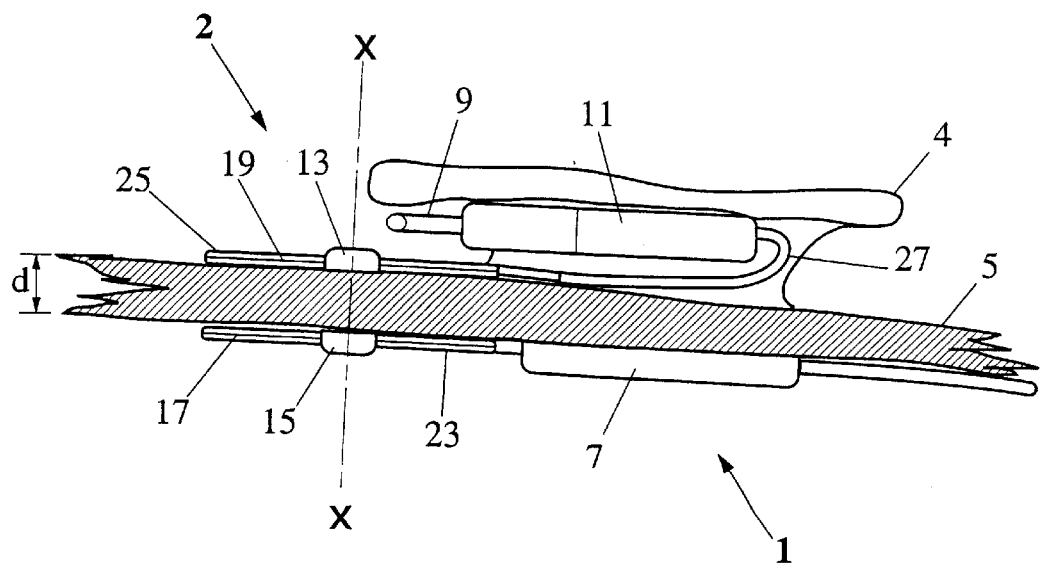
FIG. 1B shows a plan view of the arrangement of FIG. 1A.

FIGS. 1A and 1B depict the arrangement of a typical prior art transcutaneous tissue stimulating system, being a cochlear implant prosthesis operatively positioned. While the present invention will be described with reference to a two-part cochlear prosthesis it will be understood that the invention is applicable to any device which makes use of a transcutaneous inductive link featuring electromagnetically coupled coils.

The cochlear implant prosthesis comprises an internal component 1 located on a first side of partition 5, said partition being formed by the skin and flesh of an implanted patient. For the sake of clarity the width of partition 5 has been greatly exaggerated in FIG. 1A. Internal component 1 includes an electronics housing 7 to which is electrically connected receiver coil 17. Coil 17 is retained by a pliable plastic coil platform 23, which is mechanically connected to electronics housing 7, for the purpose of forming the coil into a shape that will shortly be described. Also mounted to coil platform 23 is magnet 15. It will be realised that post-implantation (as shown in FIGS. 1A, 1B) internal component 1 of the cochlear implant prosthesis is fixed relative to partition 5.

Located on the opposite (external) side of partition 5 is external component 2 comprising a circular coil 19 mounted in coil platform 25 and magnet 13 which is engaged by the coil platform. Coil platform 25 is comprised of a circular coil enclosure 14 having three spokes 16 which hold the magnet 13 in a central position. Other parts of external component 2 of the cochlear implant prosthesis are microphone 9, behind-the-ear sound processor 11, which is tucked behind the outer ear 4 of the implanted patient, and cable 27.

In operation internal magnet 15 attracts external magnet 13 forcing coil platform 25 against the external side of partition 5, i.e. the side of the implanteeÕs head. Consequently external platform 25 is held in place by static friction between it and partition 5. It will be understood that there is a strong tendency for external platform 25 to be placed so that the distance between internal magnet 15 and external magnet 13 is reduced to a minimum. Consequently the magnets typically come to be positioned so that they are lined up over each other as shown in FIGS. 1A and 1B and indicated by the line X—X.

Figure 2A:
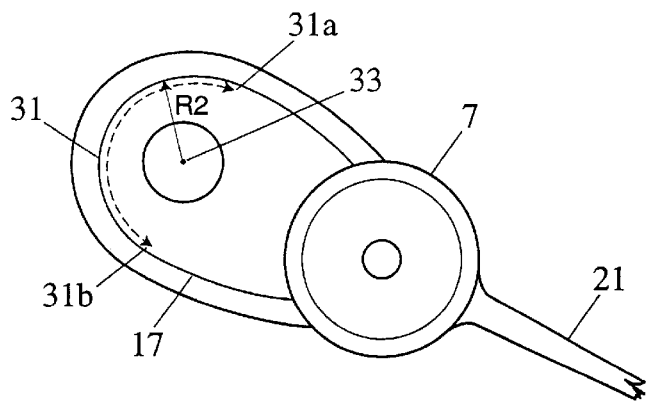
FIG. 2A shows the geometry of the coil of the internal component of the prosthesis of FIGS. 1A, 1B.
Figure 2B:
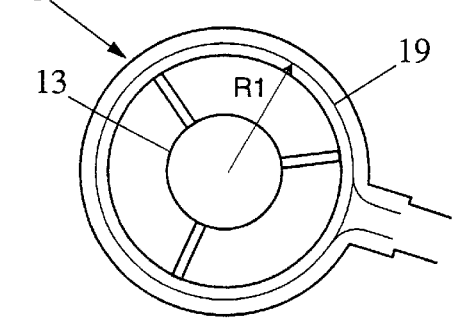
FIG. 2B shows the geometry of the coil of the external component of the prosthesis of FIGS. 1A, 1B.

With reference to FIG. 2A, it will be noted that in the prior art arrangement internal coil 17 is not completely circular but rather describes an arc 31, limited by points 31A and 31B, having a centre 33 and radius R2. With reference to FIG. 2B it is seen that the prior art external component has a circular transmitter coil 19 of radius R1. Typically R2 is approximately 75% of R1. Magnets 15 and 13 are located at the centres of arc 31 and the circle formed by coil 19 respectively.

Figure 3:
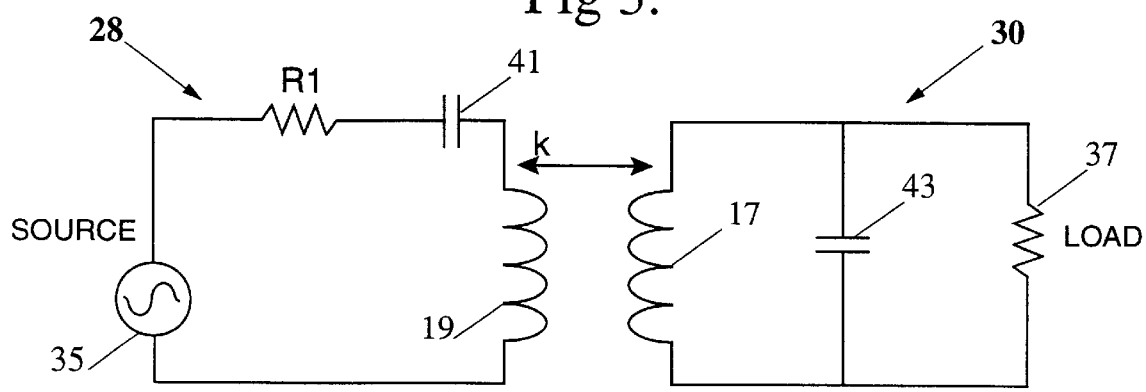
FIG. 3 shows an equivalent circuit for a prior art implantable prosthesis system.

FIG. 3 depicts an electrical circuit model of the arrangement of the cochlear implant prosthesis shown in FIGS. 1A and 1B. In the model source 35 represents the signal generating electronics housed in behind-the-ear speech processor 11 with the processing and stimulating electronics housed in receiver casing 7 being represented by load 37. Transmit coil 19 forms part of a tuned circuit 28 with capacitor 41. Similarly coil 17 and tuning capacitor 43 form a second tuned circuit 30. Each of the tuned circuits has a natural frequency of oscillation, said circuits 28, 30 being tuned so that their natural frequencies are close to each other. Moreover the two coils 19, 17 are positioned relative to each other as has previously been explained with reference to FIGS. 1A and 1B. Energy from coil 19 is transferred to coil 17 by the mutual electromagnetic or inductive coupling between the coils, said coupling being quantitatively indicated by a coefficient k. More specifically, the coupling coefficient k is indicative of the proportion of the magnetic fields linking the coils. When the coils are close the coefficient k takes a large value. As the distance d, shown in FIGS.1A and 1B, increases the value of k decreases as shown in FIG. 4.

The ratio A of the RMS voltage induced in coil 17 in response to an RMS voltage in coil 19 varies with coefficient k and distance d as illustrated in FIGS. 5A and 5B. It will be realised that the distance d corresponds to the width of partition 5 of FIG. 1. The partition width varies from patient to patient and consequently the voltage transfer ratio A also differs from patient to patient, being less than optimal in patients having either a considerably thicker or thinner partition width than usual. A ramification of this variability is that in order to ensure that an adequate voltage level is induced in coil 17, for purposes of operating the internal component of the cochlear prosthesis, the voltage applied to coil 19 must be sufficiently high to take into account patients having considerably thicker or thinner partition widths than typically encountered. As a consequence while the voltage induced in coil 17 is sufficient in patients having an atypical partition width, it is higher than required in most patients who have a typical partition and so leads to an undesirable power wastage.

Figure 6:
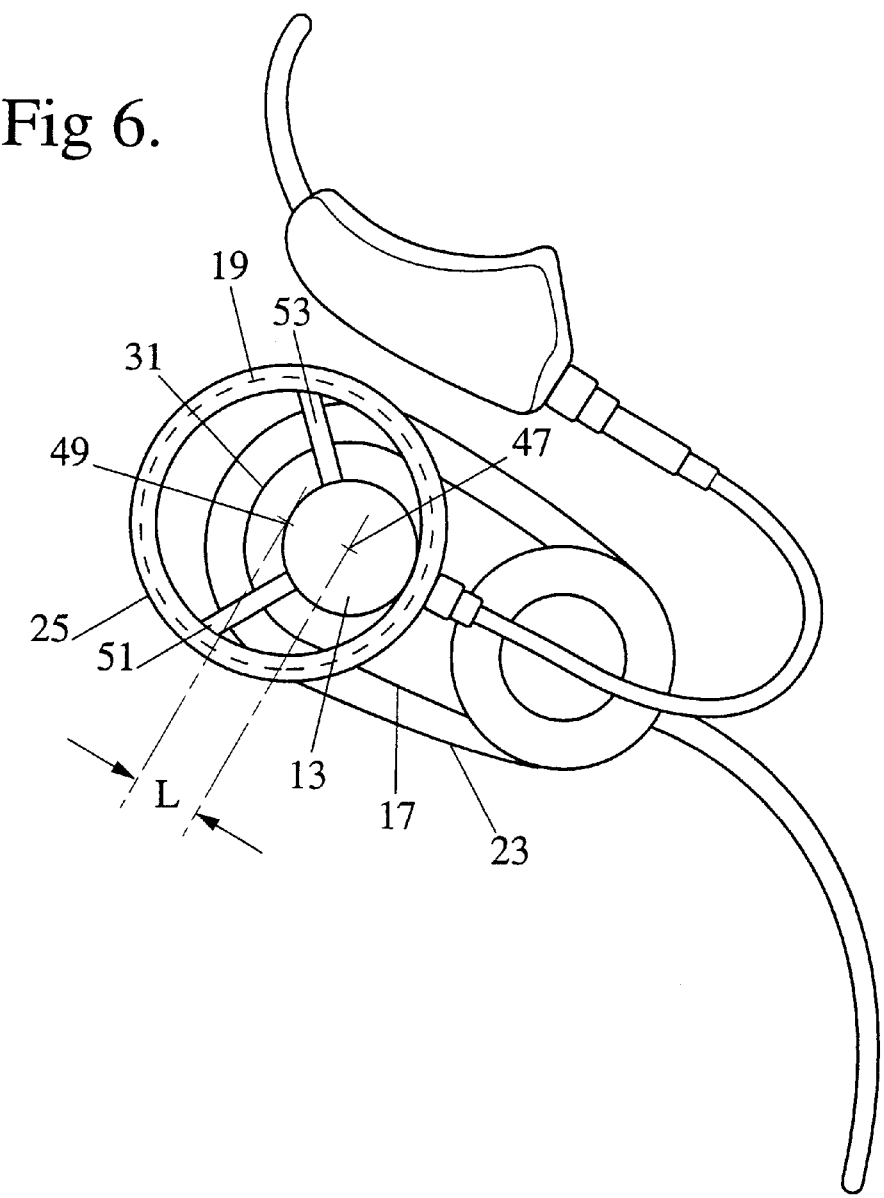
FIG. 6 depicts a coil arrangement according to the present invention.

Referring now to FIG. 6 there is illustrated an embodiment of the present invention which addresses this problem. It will be noted that the centre 47 of arc 31 of receive coil 17 has been radially offset from the centre 49 of circular transmit coil 19 by a distance L so that arc 31 and circular coil 19 are no longer concentric. The radial offsetting of the transmit and receive coil centres is accomplished by locating magnet 13 at an eccentric position relative to circular coil 19 by means of magnet platform members 51 and 53. A similar offsetting of the transmit and receive coils could also be achieved by eccentrically locating magnet 15 (not visible in FIG. 6) or indeed by eccentrically locating both magnets to some extent.

Figure 7:
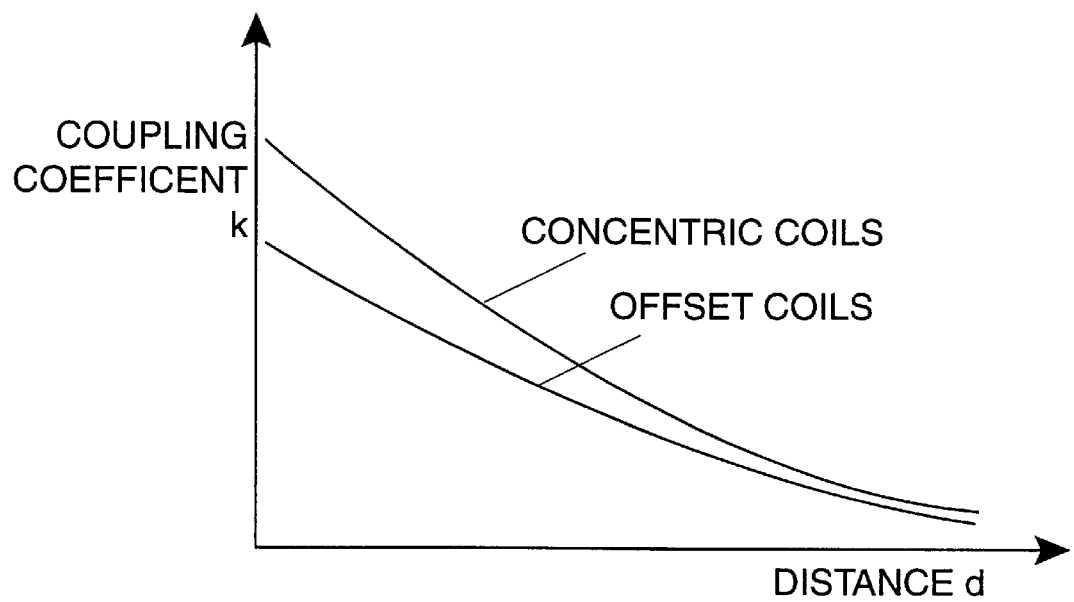
FIG. 7 shows a comparison between the coupling coefficients of concentric and offset coils as a function of distance.

The result of offsetting the receive and transmit coils as depicted in FIG. 6 is that the coefficient k decreases at a lower rate as inter-coil distance d increases than was the case in the prior art arrangement, as illustrated in FIG. 7. It will be appreciated from FIG. 7 that in the case of the offset coils of FIG. 6, coefficient k decreases at a lower rate with d than in the prior art arrangement and that this effect is most pronounced for smaller values of d.

Figure 8:
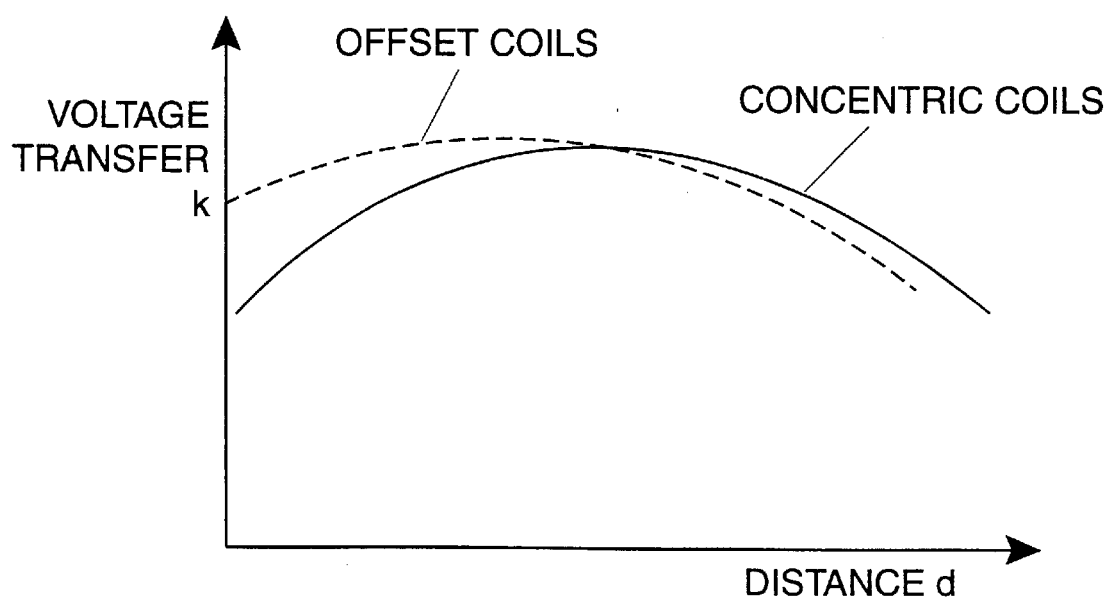
FIG. 8 shows a comparison between transfer ratios of concentric and offset coils as a function of distance.

As shown in FIG. 8, the voltage transfer A for smaller values of d is not only greater than for concentric coils but is also less variable. Thus FIGS. 7 and 8 demonstrate that the inventive intercoil arrangement reduces the voltage transfer ratioÔs sensitivity to variations in the intercoil distance d as desired.

The value of the offset L depends on the radii R1 and R2. In the examples given above, where R2 is about 75% of R1, the offset L is about 40% of R1, though it may be varied over the range of 20%–100% of R1 while still achieving the desired effect.

Figure 9:
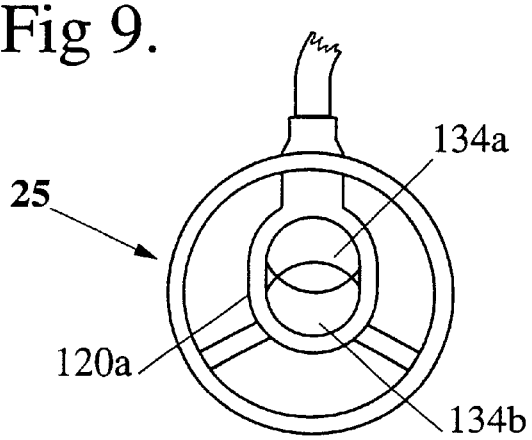
FIG. 9 shows a further embodiment of the invention which facilitates selection between two inter-coil positions.

Again with reference to FIG. 8, it will be noted that for large values of d, such as may occur in patients having very thick skin, the voltage transfer ratio associated with the inventive arrangement (shown by the dashed curve) falls off markedly. Consequently it would be advantageous if, when applied to a patient having very thick skin, the relative coil position could be adjusted from the off set position to the prior art concentric position. A configuration which allows selection between the two positions is shown in FIG. 9.

In the embodiment depicted therein coil platform 25 is provided with an elongated capsule 120A configured to locate magnet 13 in at least two possible locations, shown as 134A, 134B. When occupying the 134B position the external magnet aligns the centre of the transmit coil with the centre of the receive coil arc. Consequently the Òconcentric Ó voltage transfer ratio of FIG. 8 is selected, which is appropriate for patients having a considerably thicker-than-typical skin. Alternatively when the prosthesis is used applied to a patient having a partition of lesser thickness the eccentric magnet position 134A is preferred as in that position the more appropriate offset transfer ratio of FIG. 8 is selected.

Obviously numerous modifications can be made to the invention without departing from its scope as defined in the appended claims. For example, and not exhaustively, the shape of the coils or coil platforms may be varied without affecting the operation of the invention.

I claim:

1. A transcutaneous tissue stimulating system comprising:

a) an external portion for location on a first side of a partition, said external portion including a first coil for transmission of RF power, arranged to form an arc of a first radius and being retained by means of a first coil platform said coil platform engaging a first magnet; and b) an internal portion for location on a side opposite the first side of said partition, including a second coil for receiving RF power, arranged to form an arc of a second radius said second coil being mounted on a second coil platform said second coil platform engaging a second magnet for attraction to said first magnet;

wherein the first and second coil, platform and magnets are arranged so that upon minimising the distance between said first and second magnets the centres of the first and second arcs are radially offset.

2. The system according to claim 1 wherein said offset is 20% to 100% of the first radius.

3. The system according to claim 1 wherein said first coil describes a circle so that said first arc forms a circle.

4. The system according to claim 1, wherein said first magnet, platform and coil are arranged so that said first magnet is located at the centre of said first arc and said second magnet, platform and coil are arranged so that said second magnet is radially offset from the centre of said second arc.

5. The system according to claim 1, wherein said second magnet, platform and coil are arranged so that said second magnet is located at the centre of said second arc and said first magnet, platform and coil are arranged so that said first magnet is radially offset from the centre of said first arc.

6. A transcutaneous tissue stimulating system comprising:

a) an external portion for location on a first side of a partition, said external portion including a first coil for transmission of RF power, arranged to form an arc of a first radius and being retained by means of a first coil platform said coil platform engaging a first magnet in one of a first and a second selectable positions, said selectable positions being radially offset from each other; and b) an internal portion for location on a side opposite the first side of said partition, including a second coil for receiving RF power, arranged to form an arc of a second radius said second coil being mounted on a second coil platform said second coil platform engaging a second magnet for attraction to said first magnet;

wherein the first and second coil, platform and magnets are arranged so that when said first magnet is engaged in said first selectable position then upon minimising the distance between said first and second magnets the centres of said first and second arcs are radially co-located and when said first magnet is engaged in said second selectable position then upon minimising said distance said centres are radially offset.

7. The system according to claim 6, wherein the first of said at least two positions is the centre of said first arc and the second said position is radially offset therefrom.

8. The system according to claim 7, wherein upon said magnet being engaged in said second selectable position said centres are offset by 20% to 100% of the first radius.

9. The system according to claim 8, wherein said first coil is arranged to describe a circle so that said first arc forms a circle.

10. An implantable prosthesis comprising:

an internal component constructed and arranged to be implanted in a patient's body, said internal component including an internal coil; and an external component constructed and arranged to cooperate with said internal component to provide therapy to the patient, said external component including an external coil for transmission of energy to the internal coil.

11. The prosthesis of claim 10 wherein said coils have respective centers, said centers being offset by said predetermined displacement.

12. The prosthesis of claim 10 wherein said internal and external components exchange RF signals through said coils.

13. The prosthesis of claim 10 wherein said coils are inductively coupled.

14. The prosthesis of claim 10 wherein at least one of said coils has a coil diameter and said predetermined displacement is smaller than said diameter.

15. A cochlear implant system comprising;
an external component including a microphone for sensing ambient sounds and generating corresponding electrical signals, a signal processor for processing said electrical signals to generate stimulation signals and a transmitter for transmitting said stimulation signals, said transmitter including a transmit coil; and
an internal component constructed and arranged to be implanted into a patient, said internal component including a receiver for receiving said signals and an electrode assembly for applying stimulation signals corresponding to ambient sounds to a nerve, said receiver including a receive coil;
wherein said transmit and receive coils are offset laterally by a predetermined displacement.

16. The system of claim 15 wherein said coils extend in respective parallel planes and are offset by said predetermined displacement along said planes.

17. The system of claim 15 wherein said coils have respective centers, said centers being displaced by said predetermined displacement.

18. The system of claim 15 wherein said transmitter and receiver are constructed and arranged to exchange RF signals.

19. The system of claim 15 wherein said transmitter and receiver are constructed and arranged to be inductively coupled through said coils.

20. The system of claim 15 wherein said transmitter and receiver are positioned at a longitudinal distance and said receive and transmit coils are inductively coupled in accordance with a coupling factor, said predetermined displacement being selected to reduce variations of said coupling corresponding to variations in said longitudinal distance.

21. The system of claim 15 wherein said transmitter and receiver are positioned at a longitudinal distance and said receive and transmit coils exchange signal with a voltage ratio, said predetermined displacement being selected to minimize variations in said voltage ratio due to variations in said longitudinal distance.

22. The system of claim 15 wherein said transmitter and receiver include respective coil holder members.

23. The system of claim 22 wherein said coil holder members include permanent magnets.

24. The system of claim 22 wherein at least one of said coil holder members is arranged and constructed to hold the respective coil in one of a first and a second positions, the coil being disposed in said first position at said predetermined displacement from the other coil, said coil being disposed in said second position substantially coaxially with respect to said other coil.

25. The system of claim 15 wherein each said transmit and receive coils have a respective center and a placement magnet for positioning said coils in a facing relationship, said magnets being displaced from said centers.

26. The system of claim 25 wherein said placement magnets are arranged to position said coils with said centers being laterally offset by said predetermined displacement.

* * * * *